United States Patent [19]

Pelosi, Jr. et al.

[11] 4,035,394
[45] July 12, 1977

[54] 5-PHENYL-2-FURANYL-OXO OR-HYDROXY ALKANOIC ACIDS AND ETHYL ESTERS AS GASTRIC ACID ANTISECRETORY AGENTS

[75] Inventors: Stanford S. Pelosi, Jr.; Marvin M. Goldenberg, both of Norwich, N.Y.

[73] Assignee: Morton-Norwich Products, Inc., Norwich, N.Y.

[21] Appl. No.: 660,832

[22] Filed: Feb. 24, 1976

[51] Int. Cl.$^2$ ..................................... C07D 307/54
[52] U.S. Cl. ...................... 260/347.3; 260/347.4; 424/285
[58] Field of Search .......... 260/347.3, 347.4, 347.5

[56] References Cited

U.S. PATENT DOCUMENTS 3,962,284  6/1976  Pelosi, Jr. .................. 260/347.5

Primary Examiner—Henry R. Jiles
Assistant Examiner—Bernard Dentz
Attorney, Agent, or Firm—Anthony J. Franze

[57] ABSTRACT

Certain 5-phenyl-2-furanyl-oxo or-hydroxy alkanoic acids and ethyl esters are useful as gastric acid antisecretory agents.

7 Claims, No Drawings

5-PHENYL-2-FURANYL-OXO OR-HYDROXY ALKANOIC ACIDS AND ETHYL ESTERS AS GASTRIC ACID ANTISECRETORY AGENTS

This invention is concerned with the provision of medicinal substances particularly chemical compounds having utility as gastric acid antisecretory agents. In accordance with this objective it has been discovered that certain 5-phenyl-2-furanyl-oxo or-hydroxy alkanoic acids and ethyl esters thereof are particularly efficacious in inhibiting gastric acid output and thus find utility as medicinal agents.

The chemical compounds which have been found to be possessed of valuable gastric acid antisecretory effects consist of a small, closely related series of 5-phenyl-2-furanyl-oxo or-hydroxy alkanoic acids and ethyl esters particularly the following:

A. Ethyl 3-[5-(4-Nitrophenyl)-2-furanyl]-3-hydroxypropanoate
B. 4-[5-(4-Chlorophenyl)-2-furanyl]-4-hydroxybutanoic acid.
C. 3-[5-(2-Chlorophenyl)-2-furanyl]-3-hydroxypropanoic acid.
D. 4-[5-Chlorophenyl)-2-furanyl]-4-oxo-butanoic acid.
E. 3-[5-(2,4-Dichlorophenyl)-2-furanyl]-3-hydroxypropanioc acid.
F. Ethyl 3-[5-(4-Chlorophenyl)-2-furanyl]-3-oxopropanoate.

The methods currently preferred for preparing the compounds A–F are illustrated in the following examples.

EXAMPLE I

Ethyl 3-[5-(4-Nitrophenyl)-2-furanyl]-3-hydroxypropanoate

A. Preparation of Lithium N-Isopropylcyclohexylamide

A flamed-out flask under a nitrogen atmosphere was charged with 125 ml of a hexane solution containing 0.250 mole of n-butyllithium.

The flask was immersed in an ice bath and 37 g (0.263 mole) of N-isopropylcyclohexylamine was added dropwise over a 10 minute period. The ice bath was removed and stirring was continued for 10 additional minutes. The hexane was removed under reduced pressure with an oil pump to leave a white residual solid which was dissolved in 725 ml of tetrahydrofuran.

B. Preparation of Lithio Ethyl Acetate

The reaction flask was immersed in a dry ice-acetone bath and stirred 15 minutes to insure temperature equilibration. After this time 22 g (0.250 mole) of ethyl acetate was added over a 10 minute period. Stirring at dry ice temperature was continued an additional 15 minutes to insure the complete formation of lithio ethyl acetate.

C. Preparation of title compound

A mixture of 54 g (0.250 mole) of 5-(4-nitrophenyl)2-furancarboxaldehyde was added portionwise to the above prepared lithio ethyl acetate over a 10 minute period. The resulting mixture was stirred at dry ice-acetone temperature for an additional hour and then hydrolyzed by adding 75 ml of 20% hydrochloric acid. The reaction was allowed to warm to room temperature and a small amount of insoluble material was filtered and discarded. The organic layer was separated and dried over $MgSO_4$. The solvent was removed on a Calab evaporator yielding a residual oil which partially solidified upon standing. This solid was filtered, and washed with hexane. The filtrate was concentrated on a Calab yielding a residual oil which was extracted with refluxing cyclohexane. The cyclohexane was cooled to yield a solid which was filtered. The two solids were combined and air-dried to yield 45 g (61% overall). An analytical sample was prepared by drying a sample in the vacuum pistol at room temperature, m.p. 79°–81°.

Anal. Calcd. for $C_{15}H_{15}NO_5$: C, 59.01; H, 4.95; N, 4.59. Found: C, 59.09; H, 5.00; N, 4.56.

EXAMPLE II

4-[5-(4-Chlorophenyl)-2-furanyl]-4-hydroxybutanoic Acid

A solution of 8.4 g (0.030 mole) of the compound of Example IV, B. in 120 ml of 95% dioxane/water was treated portionwise with 2.84 g (0.075 mole) of $NaBH_4$ while maintaining the temperature below 25° by means of an ice bath. After stirring at ambient temperature for 30 minutes the reaction solution was added to ice/$H_2O$ and acidified with 10% hydrochloric acid. The resulting solid was filtered and air dried to yield 6.7 g (80%). An analytical sample was prepared by dissolving a sample in ethyl acetate (Darco), diluting with hexane and drying the resulting solid in the vacuum pistol at room temperature, m.p. 100°–101°.

Anal. Calcd. for $C_{14}H_{13}ClO_4$: C, 59.90; H, 4.67. Found: C, 59.74; H, 4.63.

EXAMPLE III

3-[5-(2-Chlorophenyl)-2-furanyl]-3-hydroxypropanoic Acid

A solution of 0.25 mole of lithio ethyl acetate in 725 ml of tetrahydrofuran was treated portionwise with 52 g (0.25 mole) of 5-(2-chlorophenyl)-2-furaldehyde, while under a nitrogen atmosphere and at the temperature of dry ice-acetone. The resulting mixture was stirred in the cold for 1 additional hr. and then 75 ml of 20% hydrochloric acid was added. The reaction was allowed to warm to room temperature. The organic layer was separated, dried over $MgSO_4$ and the solvent removed on a Calab evaporator yielding the crude ester as a residual oil.

A mixture of 87 g (0.24 mole) of the above ester, 312 ml of ethanol, 240 ml of 1 N NaOH solution and 410 ml of water was warmed at 45° for 1 hr, cooled to room temperature and then washed several times with ether. The aqueous layer was made acidic with 10% hydrochloric acid, and the resulting oil extracted with ether. The combined etheral extracts were dried over $MgSO_4$ and the ether removed on a Calab evaporator. The resulting residual oil was dissolved in toluene, and hexane was added with a solid forming. The above procedures was repeated three more times yielding 25 g (26%) of product, m.p. 53°–55°.

Anal. Calcd. for $C_{13}H_{11}ClO_4$: C, 58.55; H, 4.16. Found: C, 58.52; H, 4.11.

EXAMPLE IV

A. Methyl 4-[5-(4-Chlorophenyl)-2-furanyl]-4-oxobutanoate

To a stirring mixture of 62 g (0.50 mole) of $AlCl_3$ in 375 ml of 1,2-dichloroethane was added portionwise 75 g (0.5 mole) of 3-carbomethoxypropionyl chloride while keeping the temperature below 25° by means of an ice bath. The reaction mixture was cooled to 15° and a solution of 89 g (0.5 mole) of 5-(4-chlorophenyl)furan in 250 ml of 1,2-dichloroethane was added dropwise with HCl gas being evolved and the temperature rising to 30°. The reaction mixture was stirred at ambient temperature for 1 hour and then added to 1000 ml of ice/water. The organic layer was separated and the aqueous layer extracted with dichloromethane. The combined organic layers were washed with 1000 ml of 6% sodium carbonate solution with 1000 ml of water and dried over MgSO$_4$. The solvent was removed on a Calab evaporator yielding a residual oil which was extracted several times with refluxing hexane. The hexane extracts were cooled to yield a solid which was filtered, washed twice with 6% sodium carbonate solution, recrystallized from hexane and air dried to yield 7 g (5%). An analytical sample was prepared by drying a sample in a vacuum pistol at room temperature, m.p. 99°–100°.

Anal. Calcd. for $C_{15}H_{13}ClO_4$: C, 61.55; H, 4.48. Found: C, 61.49; H, 4.50.

B. 4-[5-(4-Chlorophenyl)-2-furanyl]-4-oxobutanoic Acid

A mixture of 2.92 g (0.01 mole) of A., 13 ml of ethanol, 10 ml of 1 N NaOH solution and 20 ml of water was stirred at 50° for 1 hr, at room temperature for 1 hour, and was then washed several times with ether. The aqueous layer was made acidic with 10% hydrochloric acid and the resulting solid was filtered. The solid was washed wih water, washed with hexane, and dried at room temperature in a vacuum pistol to yield 1.7 g (61%) of product, m.p. 142°–144°.

Anal. Calcd. for $C_{14}H_{11}ClO_4$: C, 60.33; H, 3.97. Found: C, 59.95; H, 4.02.

EXAMPLE V

3-[5-(2,4-Dichlorophenyl)-2-furanyl]-3-hydroxypropanoic Acid

A solution of 0.25 mole of lithio ethyl acetate in 725 ml of tetrahydrofuran was treated portionwise with 60 g (0.25 mole) of 5-(2,4-dichlorophenyl)-2-furaldehyde while under a nitrogen atmosphere and at a temperature of dry ice-icetone. The resulting mixture was stirred in the cold for 1 additional hr, and then 75 ml of 20% hydrochloric acid was added. The reaction was allowed to warm to room temperature. The organic layer was seperated and dried over MgSO$_4$ and the solvent was removed on a Calab evaporator yielding the crude ester as a residual oil.

A mixture of 100 g (0.24 mole) of the above ester, 300 ml of 1 N NaOH solution, 390 ml of ethanol and 600 ml of water was warmed at 45° for 1 hr. and then cooled at room temperature. The mixture was washed twice with ether and the resulting solution made acidic with 10% hydrochloric acid. The resulting oil was extracted with ether and the combined etheral extracts dried over MgSO$_4$. The solvent was removed on a Calab evaporator yielding a residual solid. This solid was recrystallized from toluene at steam bath temperature and dried at 60° to yield 36 g (49%). An analytical sample was prepared by recrystallization of a sample a second time from toluene and drying in the vacuum pistol at the temperature of refluxing CHCl$_3$, m.p. 102°–103°.

Anal. Calcd. for $C_{13}H_{10}Cl_2O_4$: C, 51.85; H, 3.31. Found: C, 51.89; H, 3.26.

EXAMPLE VI

A. ethyl 3-[5-(4-Chlorophenyl)-2-furanyl]-3-oxopropanoate

To a stirring solution of 2000 ml of diethyl carbonate in an ice bath was added portionwise 78 g of NaH. While maintaining ice bath temperature, 213 g (0.97 mole) of 5-(p-chlorophenyl)-2-furylmethyl ketone was added portionwise. The bath was removed and the reaction was stirred at ambient temperature for 1 hr and then refluxed for 4 hrs. An additional 1000 ml of diethyl carbonate was added to aid in stirring. The mixture was cooled and 130 ml of ethanol was added dropwise. The solid was filtered, washed with hexane and air dried to yield 225 g (74%).

B. Ethyl 3-[5-(4-Chlorophenyl)-2-furanyl]-3-oxopropanoate

A 50 g (0.16 mole) sample of A. was suspended in a mixture of 500 ml of ether and 500 ml of H$_2$O. The resulting mixture was acidified with concentrated hydrochloric acid. The ether layer was then separated, dried over MgSO$_4$ and concentrated on a Calab evaporator yielding a residual oil. This oil was extracted with refluxing hexane and the hexane upon cooling yielded 12.5 g (27%) of product. An analytical sample was prepared by recrystallizing a sample from hexane and drying in the vacuum piston at room temperature, m.p. 46°–47°.

Anal. Calcd. for $C_{15}H_{13}ClO_4$: C, 61.55; H, 5.88. Found: C, 61.46; H, 4.68.

The compounds described herein exhibit a salutary effect upon gastric acid secretion. Such effect is evidenced using a modified standard pylorus-ligated secretory testing procedure in the rat. Sprague-Dawley rats, weighing 180–210 g and previously fasted for 24 hours, were used. All compounds were given perorally as suspensions in 0.5% Methocel 1 hour prior to pylorus ligation. Under light ether anesthesia, the rat stomach was ligated at the pylorus region. Four hours after ligation the conscious rat was sacrificed by a chloroform overdose. The stomach was carefully excised and its content drained into a centrifuge tube. Samples were centrifuged to separate secretions from debris. Gastric fluid volume reading and determination of sample contamination, based on debris and sample color, was made. Titration was performed on a sample aliquot of 1 ml diluted to a volume of 5 ml using distilled water. The titrant used was 0.1N NaOH. Total gastric acid output in the stomach was determined by titration to pH7. A dose of 300 mg/kg p.o. of a compound was administered to a group of rats and its effect on the volume of gastric secretion and acid output compared to a control group receiving 0.5% Methocel p.o. The activity of each compound based on the degree of inhibition of gastric acid output is set forth in Table I.

Table I

| Compound of Example | % Inhibition | |
| --- | --- | --- |
| | Gastric Acid Output | Vol. of Gastric Secretion |
| I | 43.1 | 33.17 |
| II | 72.3 | 47.3 |
| III | 95.0 | 33.5 |
| IV, B | 57.1 | 40.7 |
| V | 45.4 | 3.4 |
| VI, B | 50.0 | 19.8 |

What is claimed is:

1. A compound having gastric acid antisecretory activity selected from the group consisting of:
   A. Ethyl 3-[5-(4-nitrophenyl)-2-furanyl]-3-hydroxypropanoate
   B. 4-[5-(4-chlorophenyl)-2-furanyl]-4-hydroxy butanoic acid
   C. 3-[5-(2-chlorophenyl)-2-furanyl]-3-hydropropanoic acid
   D. 4-[5-(4-chlorophenyl)-2-furanyl]-4-oxo-butanoic acid
   E. 3-[5-(2,4-dichlorophenyl)-2-furanyl]-3-hydropropanoic acid
   F. Ethyl 3-[5-(4-chlorophenyl)-2-furanyl]-3-oxopropanoate 2. The compound ethyl 3-[5-(4-nitrophenyl)-2-furanyl]-3-hydroxypropanoate.

3. The compound 4-[5-(4-chlorophenyl)-2-furanyl]-4-hydroxy butanoic acid.

4. The compound 3-[5-(2-chlorophenyl)-2-furanyl]-3-hydropropanoic acid.

5. The compound 4-[5-(4-chlorophenyl)-2-furanyl]-4-oxobutanoic acid.

6. The compound 3-[5-(2,4-dichlorophenyl)-2-furanyl]-3-hydroxypropanoic acid.

7. The compound ethyl 3-[5-(4-chlorophenyl)-2-furanyl]-3-oxopropanoate.

* * * * *